US008206758B2

(12) United States Patent
Wehrli

(10) Patent No.: US 8,206,758 B2
(45) Date of Patent: Jun. 26, 2012

(54) METHODS OF MAKING OLIVE JUICE EXTRACTS CONTAINING REDUCED SOLIDS

(75) Inventor: Christof Wehrli, Witterswil (CH)

(73) Assignee: DSM IP Assets B.V., Heerlen (NL)

( * ) Notice: Subject to any disclaimer, the term of this patent is extended or adjusted under 35 U.S.C. 154(b) by 254 days.

(21) Appl. No.: 12/674,044

(22) PCT Filed: Aug. 19, 2008

(86) PCT No.: PCT/EP2008/006790
§ 371 (c)(1), (2), (4) Date: Feb. 18, 2010

(87) PCT Pub. No.: WO2009/024318
PCT Pub. Date: Feb. 26, 2009

(65) Prior Publication Data
US 2011/0027398 A1    Feb. 3, 2011

(30) Foreign Application Priority Data

Aug. 21, 2007   (EP) ..................................... 07016344

(51) Int. Cl.
*A01N 65/00*   (2009.01)

(52) U.S. Cl. ....................................................... 424/725
(58) Field of Classification Search ................... None
See application file for complete search history.

(56) References Cited

U.S. PATENT DOCUMENTS

| 6,361,803 | B1 | 3/2002 | Cuomo et al. |
| 2002/0004077 | A1 | 1/2002 | Cuomo et al. |
| 2008/0179246 | A1 | 7/2008 | Da Ponte et al. |
| 2008/0260880 | A1 | 10/2008 | Yokota et al. |

FOREIGN PATENT DOCUMENTS

WO    WO 2004/005228    1/2004

OTHER PUBLICATIONS

International Search Report for PCT/EP2008/006790, mailed Dec. 23, 2008.
Written Opinion of the International Searching Authority for PCT/EP2008/006790, mailed Dec. 23, 2008.

*Primary Examiner* — Michael Meller
(74) *Attorney, Agent, or Firm* — Nixon & Vanderhye P.C.

(57) ABSTRACT

Solids, including fibers can be easily removed from olive juice by mixing the olive juice with a water-miscible solvent to form two phases and separating the phases. Preferably the solvent is ethanol.

20 Claims, No Drawings

METHODS OF MAKING OLIVE JUICE EXTRACTS CONTAINING REDUCED SOLIDS

This application is the U.S. national phase of International Application No. PCT/EP2008/006790 filed 19 Aug. 2008, which designated the U.S. and claims priority to Europe Application No. 07016344.9 filed 21 Aug. 2007, the entire contents of each of which are hereby incorporated by reference.

FIELD OF THE INVENTION

This invention relates to olive juice extracts containing an decreased amount of solids, and to methods of making these extracts. Olive juice extracts can be used as nutritional supplements, as they have potent antioxidant activities. Nutritional compositions containing these novel extracts are also part of this invention.

BACKGROUND OF THE INVENTION

The medicinal benefits of olive oil and olive extracts is widely being recognized. To make olive oil, the olive fruits are ground into a paste. Pressure is applied to the paste to separate the oil from the ground fruit. In addition to providing olive oil, the pressing also releases the water content of the olive fruit, which contains many water soluble phytochemicals. This water is known by a number of names, including "vegetation water, olive juice, and olive waste water". Interestingly, while olive juice and its disposal can be a problem for the olive oil producer, this olive juice can be a desirable rich source of phenolic compounds, which can have beneficial nutritional properties.

In the past, methods to concentrate the nutritional olive juice involved time consuming incubation, filtration and/or centrifugation, and/or spray drying steps. Another problem is that the usability of dried or liquid olive juice in food or dietary supplements is limited due to the smell, bitterness, and turbidity of the olive juice, as well as the low content of hydroxytyrosol, one of the active polyphenols.

It would therefore be desirable to develop a better method for producing an all-natural, hydroxytyrosol-rich, non-bitter olive juice extract which is efficient and cost-effective.

DESCRIPTION OF THE INVENTION

In accordance with this invention, new processes for making an all-natural, hydroxytyrosol-rich, non bitter olive juice extract are presented. Also as part of this invention are novel juice extract, and compositions containing this novel olive juice extracts. Thus this invention relates to a method of removing at least some of the solids present in an olive juice comprising: a) adding a water-miscible or nearly water-miscible solvent in an amount (by volume) equal to about 40-400% of the olive juice to form two phases; and b) separating the phases.

A typical olive will contain approximately 50% water, 22% oil, 19% carbohydrates, 6% cellulose, 2% proteins, and oleuropein and hydroxytyrosol (combined) 0.2%. It should be appreciated that the exact makeup of the fruit (and its subsequent extract) will vary according to the variety of olive used, the time of harvest, and even growing conditions.

Contrary to literature reports (see e.g., Briante et al, 2002, *J. Biotechn.* 93: 109-119, and Soler-Rivas et al 2000, *J Sci Food Agric* 80:1013-1023) it has been found, in accordance with this invention, that the unknown compounds which impart a bitter taste to the olive juice are neither hydroxytyrosol nor oleuropein. While not wishing to be bound by theory, they may contain a labile phenolic ester group. Regardless of the identity of the bitter compounds, they are very sensitive to base, and are not stable at higher pH.

As used throughout the specification and claims, the following definitions apply:

"HT" means hydroxytyrosol.

"Olive Juice", "Olive Waste Water" and "Vegetation Water" are terms all intended to be used interchangeably. They refer to the water phase produced during olive oil production. It is a slurry with a complex mixture of carbohydrates along with the compounds of interest, such as HT and oleuropein (which contains bound HT, and which may be subsequently broken down to yield HT).

A. Simultaneously Removing the Bitter Taste and Increasing the Amount of HT

The following step is an optional, but preferred step in the practice of this invention. Reference is made to co-pending U.S. application Ser. No. 12/674,213 filed on Jun. 6, 2011. If desired, the process can begin with the procedures described in Section B, below.

Any form of olive juice may be used as a starting material for the processes of this invention, although minor variations of the processes may be required for optimal results. Fresh juice typically containing about 85-90% water and 10-15% solid matter can be purchased and used as a starting material in the processes of this invention. Other forms of commercially available olive juice which have been filtered by the supplier to remove some or all of the solids, are also appropriate starting materials, as well. Also appropriate is olive juice which is purchased in a concentrated form (for example, 3-4×), or concentrated prior to use by simple evaporating techniques known in the art.

In other cases, the olive juice may be conveniently purchased in a stabilized, freeze dried form where citric acid has been added to stabilize it, for example, HIDROX from CreAgri (California, USA). Dried olive juice typically contains about 60% carbohydrates, 10% fibres, 10% fat, and 6% polyphenols (this includes approximately 2% hydroxytyrosol, 0.2% tyrosol and other polyphenols), and organic acids, proteins and minerals. To use this dried form as a starting material for this invention, it should be hydrated. The resulting juice is a preferred starting material.

It has been found, in accordance with one aspect of this invention, that the polyphenol concentration of any type of olive juice can be increased by maintaining the olive juice at an elevated temperature and increasing the pH to at least 6.

The elevated temperature can exist over a wide range, i.e. from about 20 degrees C. up to about 100 degrees C. The actual temperature is not especially critical, as long as it is under the boiling point of the olive juice. Preferred temperature ranges are from about 60 to about 80 degrees C., and a more preferred temperature is about 80 degrees C.

Along with the increase in the temperature, the pH of the juice should be adjusted to a higher pH than is originally present in the untreated olive juice. The adjusted pH should be in a range of about 6 to about 11, with the preferred pH being from about 7 to about 10, and a more preferred range is from about 8 to about 9. A pH above about 10 can result in the degradation of the final HT, so it is not preferred. Any basic compound capable of adjusting pH can be used: preferred compounds are NaOH, KOH, and mixtures thereof. Generally, the amount needed will vary from batch to batch, but a typical amount needed will be approximately 10-15% by weight based on the weight of the batch.

Under the conditions of the elevated temperature and pH-complex compounds which contain bound HT may break down, liberating HT. Thus, after the reactions are substantially complete, the juice will contain a higher amount of HT than the starting material. During the time that the reactions are taking place, the pH may change, and re-adjustment(s) may be required to maintain the desired pH. It is preferred to continually adjust the pH during the time of the reaction. One way of determining that the reactions are substantially complete is that the pH will remain relatively stable (i.e. relatively unchanged) for at least about ten minutes. The amount of time it will take for a batch to reach the point of stability for about 10 minutes can vary greatly depending on the individual composition of the batch. Generally, as higher the temperature and the pH the less time the reaction will take.

At this point, the partially processed olive juice no longer is bitter. Thus this invention also includes a process for removing the bitterness from an olive juice extract comprising raising the temperature and pH of the olive juice to the abovementioned conditions. At this point, the olive juice may be process as desired, using any of the known process steps in the art, or, optionally steps presented below.

B. Removal of Solids and Fibers

The starting material for this step may be the de-bittered, HT enhanced juice made in accordance with the above description A, or it may be any starting material (such as those described in Section A as suitable as starting materials for the optional step described there. Generally concentrated juice is preferred for economic reasons, but the method will work with a variety of juices. Thus, the starting material may have solids, fats (oils) and/or fibers present in it.

Typically unprocessed olive juice will contain a large amount of fine fibers. These are difficult to filter out as they tend to clog membrane filters, requiring a large amount of maintenance. It has been found, as another aspect of this invention, that fibers, residual oil and lipids, and/or other solids present in the olive juice can be agglomerated and then easily removed by a) adding a solvent in an amount (by volume) equal to about 40-400% of the olive juice or partially concentrated olive juice to form two phases; and then b) separating the two phases.

The solvent which can be employed in this process can be any solvent or mixture of solvents which is water-miscible or nearly miscible like n-butanol. Alcohols, especially C1 to C4 (or mixtures thereof) are preferred, and ethanol is particularly preferred, especially when the end product is to be used in food or as part of a medicinal or nutritional supplement product. Other solvents which can also be utilized include: acetonitrile, acetone, and glycol.

The amount of solvent is not especially critical, and will depend on the amount of water in the mixture. Usually the solvent will be needed in an amount that is at least equal to the amount of water present. For example, if ethanol is the solvent, for every 500 ml of water, about 600 ml of EtOH will be required. However, this is subject to a wide range: from about 40-400% solvent compared to the amount of water by weight, preferably 100-240%, and more preferably about 160-220% solvent compared to the amount of water. The important criteria is that enough solvent is added so that two distinct phases are formed.

The temperature of this step is not particularly critical and may range from 0 degrees Celsius to about 80 degrees Celsius, or any temperature which is less than the boiling point of the mixture. Conveniently the temperature will be between about 20 and 60 degrees C., and most conveniently is room temperature, or about 25 degrees.

At this point, two phases exist and any convenient means can be used to separate the two phases. The method of separation will depend on the actual make up of the material. For some batches, a filter can now be easily used, and/or a centrifuge. Other batches could be easily processed by simple decantation (if not too many solids were present, or if material is stuck to the wall of the vessel) or ordinary phase separation.

In another embodiment of this invention, this same process can be used with a starting olive juice which has been processed to remove fibers, but which has undergone the de-bittering/HT concentrating step described in the previous section. Addition of the solvent and separation of the resultant phases will allow separation of any precipitates which may have formed during the debittering process.

C. Recovery of the Solvent

The solvent can be recovered for re-use, if desired, making the process more economical. Evaporation is generally the easiest way to so recover the solvent. At this point, is has been found in yet another aspect of the invention, that if one chooses to employ an evaporation step to recover the solvent, then adjusting the pH of the extract to below 6, preferably below 5, will prevent unwanted foaming during the evaporation process.

At this point, the resulting non-bitter, solids-free olive juice extract, which forms another aspect of this invention can be used as is in any way desired. For example, it can be directly incorporated into a nutritional composition, for example a food or beverage composition. The food can be suitable for humans consumption, or can be an animal feed. Alternatively, it can be made into a nutritional supplement, for example, it can be formulated into capsules, tablets, or the like using known methods. Alternatively, the composition can be used in cosmetic compositions.

In other embodiments of this invention, the non-bitter, solids-free extract is spray dried or free-dried using conventional techniques to form a powder derivative, and then incorporated into a final product. Optionally, stabilizers and the like any be added to the juice prior to the drying step. The resulting powder can be directly incorporated into a nutritional composition, or it can be an animal feed. Alternatively, it can be made into a nutritional supplement; for examples it can be formulated into capsules, tablets, or the like using known methods. Alternatively, the composition can be used in cosmetic compositions.

In other embodiments of this invention, the non-bitter, solids-free extract is subjected to additional processing steps, such as de-fatting, further extraction, or distillation of the HT. Such processes may be known techniques, or the techniques as further described in co-pending U.S. application Ser. No.12/674,034 filed on Feb. 18, 2010, may be used.

The invention is now further illustrated in the following non-limiting examples.

EXAMPLES

Example 1

Starting Material

Unless otherwise stated, all %s given refer to weight percent.

Starting material was HIDROX 6% (from CreAgri, Haywood, Calif. Its content is: (in Lot 6022406002. This is freeze-dried olive juice which has been stabilized with citric acid. weight %):

| | |
|---|---|
| Carbohydrates | Approx. 60% |
| Lipids (olive oil) | Approx. 15% |
| Fibers | Approx. 10% |
| Hydroxytyrosol | 2.1% |
| Water | Approx. 2% |

Appearance:

| | |
|---|---|
| Solubility in water: | a turbid, fine suspension |
| Taste | bitter |
| Color | beige-brown powder |

Example 2

Agglomeration of Solids with Ethanol 100 g HIDROX (CreAgri, from Example 1) 6% polyphenols, and 80 ml water were added to a reaction flask in a nitrogen atmosphere. The mixture was warmed up to 80° C. and adjusted to pH 9.0, followed by stirring for 30 minutes at 80° C. at pH 9.0 with continuous addition of a total of 38 ml sodium hydroxide 10 mol/l to maintain pH. The suspension was cooled to 60° C.

The content of hydroxytyrosol increased by the base treatment to approx. 130%.

The solids where precipitated at 60° C. by addition of 200 g ethanol. The mixture was cooled, stirred at ambient for 30 minutes and filtered by a Buchner funnel. The filtercake was washed with 50 g of ethanol 70%/water 30%.

The filtrate was adjusted to pH 5 with approx. 5 ml hydrochloric acid 10 mol/l and evaporated at the rotavapor (20 mbar, 60° C.) to recover the ethanol, the non volatile residue 33.5 g.

Content [w %]: 7.4% hydroxytyrosol, 0.8% tyrosol.
Yield: 119% of the initial hydroxytyrosol
The extract is not bitter at 1 mg/ml water

Example 3

In Table 1, below, "yield %" refers to the content of HT in the dried filtrate [w %]. Yield [w %] is based on the initial content of the starting material, HIDROX 6%.

TABLE 1

Ethanol Needed for the agglomerations of solids from hydrolyzed olive juice

| | Agglomeration | | HT in filtrate | |
|---|---|---|---|---|
| pH | with ethanol [m]* | Filtration | w % | yield % |
| 3.5 | ~3 | slow | 4.2% | 132% |
| 5.0 | ~2.3 | rapid | 7.2% | 128% |
| 6.5 | ~1.1 | rapid** | 8.9% | 126% |
| 8.0 | ~0.6 | rapid** | 8.1% | 108% |

*Agglomeration was at ambient of a 50% solution of HIDROX (see Ex. 1) in water hydrolyzed at 80° C. pH = 9. pH was adjusted with conc. HCl at RT. [m] = amounts of ethanol: 50% solution. [w/w]
Filterability and coagulation can be adjusted by the amount of ethanol (optimum different for each pH. The dried precipated mass contained 0.1-0.4% HT

Example 4

100 g HIDROX 6% polyphenols (CreAgri, Example 1) and 80 ml water were added to a reaction flask in an inert gas atmosphere. The mixture was warmed up to 60° C. under a nitrogen blanket and adjusted to pH6.0 followed by stirring for 30 minutes at 60° C. at pH 6.0 with continuous addition of a total of 36 ml sodium hydroxide 10 mol/l to maintain pH.

The content of hydroxytyrosol increased by the base treatment to approx. 115%.

The solids where precipitated at 60° C. by addition of 240 g ethanol. The mixture was cooled, stirred at ambient for 30 minutes and filtered by a Buchner funnel. The filtercake was washed with 50 ethanol 70%/water 30%

The filtrate was evaporated at the rotavapor (20 mbar, 60° C.) to recover the ethanol. We recovered: 33.5 g residue. Content [w %]: 6.3% hydroxytyrosol, 0.7% tyrosol. The residue is slightly bitter at 1 mg/ml water

Example 5

The following samples where made in accordance with the above Examples 100 g HIDROX 6% (starting material, Example 1) was mixed with 100 g water to give a 50% solution. pH was adjusted to pH 9 at 80° C. with 10 m sodium hydroxyde. After approximately 30 minutes at 80° C., hydroxytyrosol which was in bound form is liberated, and the yield increases (theoretical yield is approx. 135%). With increasing pH, less ethanol is needed to agglomerate the particles, as described in the Table, below. Too little ethanol will not agglomerate the particles enough to precipitate efficiently to form a easily removable part. Higher amounts of ethanol results in a higher yield The highest concentration of hydroxytyrosol in the filtrates resulted at a pH 8-9. For a 50% solution of olive juice, about the same amount of ethanol seems optimal.

| Hydrolysis | | | | | |
|---|---|---|---|---|---|
| pH | pH 3.5 | pH 8.0 | pH 8.0 | pH 9.0 | pH 9.0 |
| temp | 60° C. | 80° C. | 80° C. | 80° C. | 80° C. |
| Agglomeration | | | | | |
| pH | pH 8 | pH 6.5 | pH 8 | pH 8 | pH 8 |
| Ethanol | 120 g | 188 g | 210 g | 165 g | 215 g |
| | RT | 60° C. | 60° C. | RT | 60° C. |
| Soluble Residue [g] | 36.4 g | 32.0 g | 32.9 g | 33.9 g | 31.6 g |
| HT [w %] | 5.34% | 7.17% | 7.24% | 7.22% | 7.64% |
| Yield [w %] | 92.6% | 109% | 113% | 117% | 115% |
| Bitterness at 1 mg/ml | Bitter | Sl. bitter | Not bitter | Not bitter | Not bitter |

Example 6

243 g of a commercially available olive juice extract which has been processed by the provider to remove fibers (content=0.89% hydroxytyrosol) was concentrated in a vacuum to 190 g. In a reaction flask under an atmosphere of nitrogen, the concentrate was heated to 80° C. and pH was adjusted to 8.0, followed by stirring for 30 minutes at 80° C. at pH 8.0 with continuous addition of a total of 24 ml sodium hydroxide 10 mol/l to maintain pH.

To the dark colored mixture was added 280 g ethanol to make the precipitate. The mixture was cooled and stirred at ambient for 1 h. The upper solution was decanted from the precipitate and evaporated at the rotavapor to recover the ethanol. The nonvolatile residue was 78 g. Content [w %]:

2.6% hydroxytyrosol, 0.6% tyrosol. Yield: 93% of the initial hydroxytyrosol. The residue is not bitter at 1 mg/ml water.

The invention claimed is:

1. A method of removing at least some of the solids present in an olive juice consisting essentially of:
   (a) adding a pH adjuster to the olive juice to obtain a pH of at least 6;
   (b) adding to the olive juice at least one water-miscible or nearly water-miscible solvent selected from the group consisting of methanol, ethanol, propanol, butanol, acetonitrile, acetone and glycol in an amount equal to about 40-200% by volume of the olive juice to form two phases; and
   (c) separating the two phases and recovering the phase containing an olive juice which has at least some of the solids removed.

2. The method according to claim 1, wherein the solvent is ethanol.

3. The method according to claim 1 wherein step (c) comprises at least one step selected from the group consisting of a filtering step, a centrifugation step, a decanting step, and a step of removing a layer of the two phases.

4. A method of removing at least some of the solids present in an olive juice consisting essentially of:
   (a) adding a pH adjuster to the olive juice to obtain a pH of at least 6;
   (b) adding to the olive juice at least one water-miscible or nearly water-miscible solvent selected from the group consisting of methanol, ethanol, propanol, butanol, acetonitrile, acetone and glycol in an amount equal to about 40-200% by volume of the olive juice to form two phases;
   (c) separating the two phases and recovering the phase containing an olive juice which has at least some of the solids removed; and
   (d) recovering the solvent of step (b).

5. The method according to claim 4 wherein step (d) is practiced by evaporating the solvent while maintaining a pH below 6.

6. The method of claim 1 or 4, wherein step (a) is practiced by maintaining the olive juice at an elevated temperature and increasing the pH to at least 6 by adding the pH adjuster until the polyphenol concentration of the olive juice is increased.

7. The method according to claim 1, wherein the solids present in the olive juice are not fibres.

8. The method according to claim 6, wherein the elevated temperature is from about 20 degrees to 100 degrees C., and the pH is from about 6 to about 10.

9. The method according to claim 8, wherein the elevated temperature is maintained until the pH remains unchanged for at least about 10 minutes.

10. The method according to claim 6, wherein step (a) is practiced by adding NaOH, KOH or mixtures thereof as the pH adjuster to the olive juice.

11. The method according to claim 9, wherein the temperature is about 60-90° C. and the pH is about 7-9.

12. A method of removing at least some of the solids present in an olive juice consisting essentially of:
   (a) adding a pH adjuster to the olive juice to obtain a pH of at least 6;
   (b) adding to the olive juice at least one water-miscible or nearly water-miscible solvent selected from the group consisting of methanol, ethanol, propanol, butanol, acetonitrile, acetone and glycol in an amount equal to about 40-200% by volume of the olive juice to form two phases;
   (c) separating the two phases and recovering the phase containing an olive juice which has at least some of the solids removed; and
   (d) freeze drying or spray drying the olive juice.

13. The method according to claim 4 or 12, wherein the solvent is ethanol.

14. The method according to claim 4 or 12, wherein step (c) comprises at least one step selected from the group consisting of a filtering step, a centrifugation step, a decanting step, and a step of removing a layer of the two phases.

15. The method of claim 12, wherein step (a) is practiced by maintaining the olive juice at an elevated temperature and increasing the pH to at least 6 by adding the pH adjuster until the polyphenol concentration of the olive juice is increased.

16. The method according to claim 12, wherein the solids present in the olive juice are not fibres.

17. The method according to claim 15, wherein the elevated temperature is from about 20 degrees to 100 degrees C., and the pH is from about 6 to about 10.

18. The method according to claim 17, wherein the elevated temperature is maintained until the pH remains unchanged for at least about 10 minutes.

19. The method according to claim 15, wherein step (a) is practiced by adding NaOH, KOH or mixtures thereof as the pH adjuster to the olive juice.

20. The method according to claim 18, wherein the temperature is about 60-90° C. and the pH is about 7-9.

* * * * *